(12) United States Patent
Donaldson et al.

(10) Patent No.: US 12,410,293 B2
(45) Date of Patent: Sep. 9, 2025

(54) SYSTEMS AND METHODS RELATING TO MEDICAL APPLICATIONS OF INVERSE THERMOSENSITIVE POLYMER FOAM FORMULATIONS

(71) Applicant: Critical Innovations LLC, Lawndale, CA (US)

(72) Inventors: Ross I. Donaldson, Lawndale, CA (US); Jonathan Armstrong, Inglewood, CA (US); Oliver Buchanan, Inglewood, CA (US); John Cambridge, Inglewood, CA (US); Timothy Fisher, Lawndale, CA (US); Nely Cristerna, Lawndale, CA (US)

(73) Assignee: Critical Innovations LLC, Lawndale, CA (US)

( * ) Notice: Subject to any disclaimer, the term of this patent is extended or adjusted under 35 U.S.C. 154(b) by 153 days.

(21) Appl. No.: 18/485,800

(22) Filed: Oct. 12, 2023

(65) Prior Publication Data
US 2024/0158596 A1    May 16, 2024

Related U.S. Application Data

(60) Provisional application No. 63/423,308, filed on Nov. 7, 2022.

(51) Int. Cl.
*C08J 9/14* (2006.01)
*A61L 26/00* (2006.01)

(52) U.S. Cl.
CPC ............ *C08J 9/146* (2013.01); *A61L 26/0019* (2013.01); *A61L 26/0076* (2013.01); *A61L 26/0085* (2013.01); *C08J 2371/02* (2013.01)

(58) Field of Classification Search
CPC ........ A61K 9/0014; A61K 9/12; A61K 9/124; A61K 47/10; A61L 26/0019; A61L 26/0076; A61L 26/0085; B65D 83/285; B65D 83/382; B65D 83/42; B65D 83/46; B65D 83/64; C08J 9/146; C08J 2371/02
See application file for complete search history.

(56) References Cited

U.S. PATENT DOCUMENTS

| | | |
|---|---|---|
| 4,474,752 A | 10/1984 | Haslam et al. |
| 6,187,290 B1 | 2/2001 | Gilchrist et al. |
| 6,316,011 B1 | 11/2001 | Ron et al. |
| 7,229,433 B2 | 6/2007 | Mullen |
| 8,062,282 B2 | 11/2011 | Kolb |
| 8,198,365 B2 | 6/2012 | Ingenito |
| 8,497,408 B2 | 7/2013 | Winek et al. |
| 8,668,899 B2 | 3/2014 | Dowling et al. |
| 8,828,050 B2 | 9/2014 | Gregory et al. |
| 9,283,278 B2 | 3/2016 | Rodeheaver et al. |
| 9,616,088 B2 | 4/2017 | Diehn et al. |
| 9,884,136 B2 | 2/2018 | Rodeheaver et al. |
| 10,111,834 B2 | 10/2018 | Laub |
| 10,456,416 B2 | 10/2019 | Koller et al. |
| 10,857,100 B2 | 12/2020 | Laub |
| 11,207,060 B2 | 12/2021 | Donaldson et al. |
| 2002/0122771 A1 | 9/2002 | Holland et al. |
| 2003/0095945 A1 | 5/2003 | Levey et al. |
| 2003/0203044 A1 | 10/2003 | Moravec |
| 2004/0013715 A1 | 1/2004 | Winek et al. |
| 2005/0008610 A1 | 1/2005 | Schwarz et al. |
| 2005/0064021 A1 | 3/2005 | Rippon et al. |
| 2005/0147585 A1 | 7/2005 | Schwarz |
| 2006/0100370 A1 | 5/2006 | Wellisz et al. |
| 2006/0193899 A1 | 8/2006 | Sawhney |
| 2007/0191768 A1 | 8/2007 | Kolb |
| 2008/0031847 A1 | 2/2008 | Cohn et al. |
| 2008/0181952 A1 | 7/2008 | Vogel |
| 2008/0208163 A1 | 8/2008 | Wilkie |
| 2009/0041824 A1 | 2/2009 | Zugates et al. |
| 2009/0254195 A1 | 10/2009 | Khairkhahan et al. |
| 2009/0286886 A1 | 11/2009 | Fisher et al. |
| 2011/0087207 A1 | 4/2011 | Vogel et al. |
| 2011/0202016 A1 | 8/2011 | Zugates et al. |

(Continued)

FOREIGN PATENT DOCUMENTS

| | | | |
|---|---|---|---|
| CA | 2394569 A1 | * | 6/2001 |
| GB | 1561423 A | | 2/1980 |

(Continued)

OTHER PUBLICATIONS

CA 2394569 A1—English Translation (Year: 2001).*
Zhao Y et al: "Engineering novel topical foams using hydrofluroalkane emulsions stabilised with pluronic surfactants", European Journal of Pharmaceutical Sciences, Elsevier, Amsterdam, NL, vol. 37, No. 3-4 Jun. 28, 2009 (Jun. 28, 2009), pp. 370-377.
European Search Report from EPO regarding Application No. EP 23168595 dated Sep. 20, 2023.

(Continued)

*Primary Examiner* — John M Cooney
(74) *Attorney, Agent, or Firm* — MERCHANT & GOULD P.C.

(57) ABSTRACT

Disclosed herein is a pressurized therapeutic composition configured to be stored in a valved container designed to maintain an inverse thermosensitive polymer foam composition under pressure and dispense the composition upon opening the valve thereof. After the composition is dispensed from the container the evaporation of an expanding component (e.g., compressed gas or volatile liquid) can cause the inverse thermosensitive polymer solution to foam. The reduced pressure produced from dispensing the inverse thermosensitive polymer solution can reduce its temperature so as to facilitate distribution in a more liquid foam form. The inverse thermosensitive polymer solution can undergo a reverse phase change from a liquid to a gel upon warming (e.g., once dispensed onto or into a body part).

15 Claims, 4 Drawing Sheets

(56) References Cited

U.S. PATENT DOCUMENTS

| | | |
|---|---|---|
| 2011/0294760 A1 | 12/2011 | Bahulekar et al. |
| 2012/0087872 A1 | 4/2012 | Tamarkin |
| 2012/0107439 A1 | 5/2012 | Sharma et al. |
| 2012/0265287 A1 | 10/2012 | Sharma et al. |
| 2013/0110066 A1 | 5/2013 | Sharma et al. |
| 2013/0158589 A1 | 6/2013 | Cohn et al. |
| 2013/0317418 A1 | 11/2013 | Freyman et al. |
| 2014/0271531 A1 | 9/2014 | Freyman et al. |
| 2014/0271533 A1 | 9/2014 | Freyman et al. |
| 2014/0316012 A1 | 10/2014 | Freyman et al. |
| 2016/0256170 A1 | 9/2016 | Busold et al. |
| 2016/0271293 A1 | 9/2016 | Zugates et al. |
| 2017/0216480 A1 | 8/2017 | Rodeheaver et al. |
| 2018/0169012 A1 | 6/2018 | Laub |
| 2023/0064184 A1 | 3/2023 | Laub |

FOREIGN PATENT DOCUMENTS

| | | |
|---|---|---|
| WO | 2009090558 A2 | 7/2009 |
| WO | 2022/226300 A1 | 10/2022 |

OTHER PUBLICATIONS

Extended European Search Report from EPO regarding Application No. EP 19163317 dated Aug. 2, 2019.
Extended European Search Report from EPO regarding Application No. EP 23207248.8 dated Jan. 8, 2024.

\* cited by examiner

| | | | Polymer Solution | | | | | | | | | | | | | | |
|---|---|---|---|---|---|---|---|---|---|---|---|---|---|---|---|---|---|
| | | | Solvent (w/w) | Polymer (w/w) | | Humectant (w/w) | Buffer System | | Antibiotics (g of base per kg of foam) | | | | Preservative (w/w) | Other | | | Expanding Gas |
| Embodiment Example | Sterile | Gel Point (C) | Water | P188 | P407 | Glycerin | Buffer | Final pH | Vancomycin | | Tobramycin | | Phenoxyethanol | Hemostatic? | Analgesic? | Mucoadhesive | Antifungal? | |
| 1 | Y | 36 | 58.5% | 42.5% | | | No | | | | | | No | | | | | 10.0% |
| 2 | Y | 25 | 58.5% | 30.0% | | | No | | | | | | No | | | | | 10.0% |
| 3 | Y | 25 | 58.5% | 60.0% | | | No | | | | | | No | | | | | 10.0% |
| 4 | N | 17.4 | 75.0% | | 25.0% | | Yes | 6.50 | | | | | Yes | | | | | 10.0% |
| 5 | N | 13.5 | 70.0% | | 17.5% | 12.5% | Yes | 6.50 | | | | | Yes | | | | | 10.0% |
| 6 | Y | ? | 75.0% | | 20.0% | | Yes | 7.00 | | | | | No | | | | | 2.5% |
| 7 | Y | 29 | 72.1% | 5.0% | 20.0% | | Yes | 6.50 | 3.60 | 0.4% | 0.89 | 0.1% | No | | | | | 2.5% |
| 8 | N | 13.5 | 70.0% | | 17.5% | 12.5% | Yes | 6.50 | 37.30 | 3.7% | 9.32 | 0.9% | No | | | | | 10.0% |
| 9 | N | 17.4 | 75.0% | | 25.0% | | Yes | 6.50 | 18.00 | 1.8% | 4.50 | 0.5% | Yes | | | | | 10.0% |
| 10 | N | 17.4 | 75.0% | | 25.0% | | Yes | 6.50 | 3.60 | 0.4% | 0.89 | 0.1% | Yes | | | | | 10.0% |
| 11 | N | 13.5 | 70.0% | | 17.5% | 12.5% | Yes | 6.50 | 3.60 | 0.4% | 0.89 | 0.1% | Yes | | | | | 10.0% |
| 12 | N | 13.5 | 70.0% | | 17.5% | 12.5% | Yes | 6.50 | | | | | Yes | | | | | 10.0% |
| 13 | N | 13.5 | 70.0% | | 17.5% | 12.5% | Yes | 6.50 | | | | | Yes | | | | | 10.0% |
| 14 | N | 13.5 | 70.0% | | 17.5% | 12.5% | Yes | 6.50 | | | | | Yes | | | | | 10.0% |
| 15 | N | 13.5 | 70.0% | | 17.5% | 12.5% | Yes | 6.50 | | | | | Yes | | | | | 10.0% |
| 16 | N | 13.5 | 70.0% | | 17.5% | 12.5% | Yes | 6.50 | | | | | Yes | | | | | 10.0% |
| 17 | Y | ? | 75.0% | | 20.0% | | Yes | 7.00 | | | | | No | | | | | 2.5% |
| 18 | Y | ? | 75.0% | | 20.0% | | Yes | 7.00 | | | | | No | | | | | 2.5% |
| 19 | Y | ? | 75.0% | | 20.0% | | Yes | 7.00 | 50.00 | 5.0% | 14.00 | 1.4% | No | Yes | | | | 2.5% |
| 20 | Y | 29 | 72.1% | 5.0% | 20.0% | | Yes | 6.50 | 37.30 | 3.7% | 9.32 | 0.9% | No | Yes | | | | 2.5% |
| 21 | Y | 29 | 72.1% | 5.0% | 20.0% | | Yes | 6.50 | 37.30 | 3.7% | 9.32 | 0.9% | No | | | | | 2.5% |
| 22 | Y | 29 | 72.1% | 5.0% | 20.0% | | Yes | 6.50 | 37.30 | 3.7% | 9.32 | 0.9% | No | | | | | 2.5% |
| 23 | Y | 29 | 72.1% | 5.0% | 20.0% | | Yes | 6.50 | 37.30 | 3.7% | 9.32 | 0.9% | No | | Yes | | | 10.0% |
| 24 | N | 13.5 | 70.0% | | 17.5% | 12.5% | Yes | 6.50 | 18.00 | 1.8% | 4.50 | 0.5% | Yes | | Yes | | | 10.0% |
| 25 | N | 13.5 | 70.0% | | 17.5% | 12.5% | Yes | 6.50 | 18.00 | 1.8% | 4.50 | 0.5% | Yes | | | | | 10.0% |
| 26 | N | 13.5 | 70.0% | | 17.5% | 12.5% | Yes | 6.50 | 18.00 | 1.8% | 4.50 | 0.5% | Yes | Yes | Yes | | | 10.0% |
| 27 | N | 13.5 | 70.0% | | 17.5% | 12.5% | Yes | 6.50 | 18.00 | 1.8% | 4.50 | 0.5% | Yes | Yes | Yes | | | 10.0% |
| 28 | N | 13.5 | 70.0% | | 17.5% | 12.5% | Yes | 6.50 | 18.00 | 1.8% | 4.50 | 0.5% | Yes | | Yes | | Yes | 10.0% |
| 29 | N | 13.5 | 70.0% | | 17.5% | 12.5% | Yes | 6.50 | 18.00 | 1.8% | 4.50 | 0.5% | Yes | | | | | 10.0% |
| 30 | N | 28 | 74.0% | 8.0% | 18.0% | | Yes | 6.50 | 3.60 | 0.4% | 0.89 | 0.1% | No | | | | | 10.0% |
| 31 | Y | 36 | 58.5% | 42.5% | | | Yes | 7.00 | | | | | Yes | | | | | 10.0% |
| 32 | N | 17.5 | 80.0% | | 20.0% | | Yes | 6.50 | 3.60 | 0.4% | 0.89 | 0.1% | No | | | Yes | Yes | 10.0% |
| 33 | Y | 20.7 | 79.5% | | 20.0% | | Yes | 7.00 | | | | | Yes | | | Yes | | 2.5% |
| 34 | N | 20.7 | 79.5% | | 20.0% | | Yes | 7.00 | | | | | Yes | | | | | 2.5% |

FIG. 4

SYSTEMS AND METHODS RELATING TO MEDICAL APPLICATIONS OF INVERSE THERMOSENSITIVE POLYMER FOAM FORMULATIONS

COMMONLY OWNED APPLICATIONS

U.S. Pat. No. 11,207,060 titled Systems and Methods Relating to Medical Applications of Synthetic Polymer Formulations, having at least one of the same inventors, is hereby incorporated by reference herein in its entirety.

This invention was made with government support under contract W81XWH-22-C-0013, "Succor Combat Foam for Advanced Wound Care of Traumatized Tissue," issued by USA MED RESEARCH ACQ ACTIVITY. The government has certain rights in the invention.

TECHNICAL FIELD

The present disclosure relates generally to systems, methods, and/or compositions relating to the production and/or delivery of synthetic polymer foam. Under some embodiments, the present disclosure relates specifically to the medical field and the delivery of synthetic polymer foam to the body.

BACKGROUND

Synthetic polymer compositions have been developed to achieve a wide range of therapeutic objectives, including hemostasis, analgesia, antifungal, antibacterial, antimicrobial, environmental stabilization (e.g., pH regulation), wound healing, regeneration of wounded tissue, immune modulation, and inhibition of biofilm. The therapeutic benefit may derive from intrinsic properties of the synthetic polymer itself and/or from the inclusion of bioactive and/or pharmaceutical agents.

For a great many of the uses described above, it is desirable for any therapeutic composition to remain in contact with the wound surface for a sustained period after application, for example for a period of several hours or days. This is commonly achieved by formulating the composition as a viscous cream, ointment, or gel. However, such viscous formulations can be difficult and time-consuming to apply topically to wounds on the body surface and are generally unsuitable for use in deep wounds or body cavities.

Some therapeutic compositions are based upon aqueous synthetic polymer solutions that exhibit inverse thermosensitive properties, wherein the solution undergoes a temperature dependent phase transition that results in an increased viscosity as the temperature rises, and a decrease in viscosity at cooler temperatures.

For example, the prior art discloses multiple uses of inverse thermosensitive polymers for the delivery of different pharmaceutical agents. These include U.S. Pat. No. 4,474,752 to Haslam et al. and U.S. Pat. No. 6,316,011 B1 to Ron et al., and U.S. Patent Publication No. 2011/0294760 A1 to Bahulekar et al. These additionally include U.S. Patent Publication No. 2005/0008610 A1 to Schwarz et al., 2005/0147585 A1 to Schwarz, 2011/0087207 A1 to Vogel et al, and 2008/0181952 A1 to Vogel et al. Additionally, U.S. Patent Publication No. 2007/0191768 A1 to Kolb (with related U.S. Pat. No. 8,062,282), 2008/0208163 A1 to Wilkie, and 2008/0031847 A1 to Cohn et al. (with related U.S. Patent Publication No. 2013/0158589). However, all of these describe the use of inverse thermosensitive polymers as gels, sprays, or pads, which may be difficult to spread over a given surface area and/or volume.

Additionally, U.S. Pat. Nos. 8,871,248 B2, 9,283,278 B2, 9,603,966 B2, 9,884,136 B2, and US 2017/0216480 A1 to Rodeheaver et al., as well as U.S. Pat. No. 5,635,540 to Edlich et al. and U.S. Pat. No. 10,456,416 B2 to Koller et al, describe at times the use of surface active agent polymers (i.e., substances capable of reducing the surface tension of a material), some of which are inverse thermosensitive polymers, in combination with other bioactive agents and/or pharmaceuticals. However, all of these describe the use of such polymers as gels, sprays, or pads, which may be difficult to spread over a given surface area and/or volume.

Finally, U.S. Patent Nos. 2018/0169012 A1 to Laub describes a medical foam for delivering an active agent to a body cavity of a patient. In some embodiments, this includes poloxamers, including a biocompatible composition of 10 wt % to 30 wt % poloxamer in water. However, this disclosure is tailored for intracavitary use inside the body of a patient and does not describe a foam for topical use on intact or damaged skin (e.g., burns, abrasions, cuts, scrapes, denuding tissue injuries, surgical incisions, venous ulcers, diabetic ulcers, arterial ulcers, pressure ulcers, radiation ulcers, traumatic wounds, non-healing wounds, complicated non-healing wounds and the like and/or combinations thereof).

Each of the patents and published patent applications mentioned above are hereby incorporated by reference.

SUMMARY

The present disclosure overcomes and substantially alleviates the deficiencies in the prior art by providing improved systems and methods relating to inverse thermosensitive polymer foam formulations. In various embodiments, the present disclosure is a pressurized therapeutic composition configured to be stored in a valved container designed to maintain an inverse thermosensitive polymer foam composition under pressure and dispense the composition upon opening the valve thereof. Under many embodiments, after the composition is dispensed from the container the evaporation of an expanding component (e.g., compressed gas or volatile liquid) causes the inverse thermosensitive polymer solution to foam. Under many embodiments, the reduced pressure produced from dispensing the inverse thermosensitive polymer solution reduces its temperature so as to facilitate distribution in a more liquid foam form. Under many embodiments, the inverse thermosensitive polymer solution undergoes a reverse phase change from a liquid to a gel upon warming (e.g., once dispensed onto or into a body part).

The present application describes synthetic polymer formulations which are especially advantageous for the treatment of traumatic injuries and acute and chronic wounds, including but not limited to, acute injuries such as burns, abrasions, cuts, scrapes, denuding tissue injuries, surgical incisions, wounds from chemical and/or biological weapon agents (e.g., sulfur mustard, vesicants, nerve agents), other traumatic wounds, or combinations thereof, and also chronic wounds such as venous ulcers, diabetic ulcers, arterial ulcers, pressure ulcers (e.g., decubitus ulcers), radiation ulcers, traumatic wounds, non-healing wounds, complicated non-healing wounds and the like and/or combinations thereof. For some of these medical problems synthetic polymers are applied topically, while for others synthetic polymers are deployed into the body (e.g., into a wound, a body cavity or potential space, or into an organ).

The therapeutic compositions disclosed in the present application are based upon aqueous synthetic polymer solutions that exhibit inverse thermosensitive properties, wherein the solution undergoes a temperature-dependent phase transition that results in an increased viscosity as the temperature rises, and a decrease in viscosity at cooler temperatures. For the synthetic polymer compositions disclosed herein, in many embodiments this phase-shift is fully thermo-reversible (i.e., reversible with change in temperature) and is due not to a chemical reaction, but rather to the innate properties of the polymer solution. The disclosed compositions have the following advantages: 1) ease of application due to the low initial viscosity; 2) enhanced coverage due to expansion into a foam; and 3) prolonged retention on wound surfaces due to the thermally induced increase in viscosity upon contact with the body. Such compositions and their advantages have not previously been known.

Under various embodiments, the inverse thermosensitive polymer foam formulation includes one or more types of inverse thermosensitive polymer. Under many embodiments, the inverse thermosensitive polymer solution undergoes a reverse phase change from a liquid to a gel upon warming.

Under several embodiments, the inverse thermosensitive polymer foam formulation comprises a solution of one or more copolymers of ethylene oxide (EO) and propylene oxide (PO) (e.g., in an aqueous solution). Such copolymers may be a random or block copolymer of EO and PO having an average molecular mass of about 1 kg/mol to about 100 kg/mol, and a mass ratio of EO to PO of between 5:95 to 95:5. In some of these embodiments, the block copolymer is a poloxamer. Poloxamers are linear A-B-A triblock copolymers of EO and PO having the general formula (EO)x(PO)y(EO)x, where x and y represent the number of EO and PO monomer units in the block. Different poloxamers having a molecular mass in the range of about 1 kg/mol to about 15 kg/mol and EO:PO ratios by mass of between 8:2 and 1:9 are commercially available, (e.g., PLURONIC® copolymers from BASF). In certain embodiments, the block copolymer is a poloxamer produced in NF grade for medical applications, and which is approved for pharmaceutical use. Examples include poloxamers P188, P237, P338, and P407, also known as Pluronic® F68, F87, F108, and F127.

In some embodiments, the inverse thermosensitive polymer foam formulation comprises a solution of one or more polyol copolymers (e.g., poloxamer, meroxapol, poloxamine). Examples of such polyol copolymers are listed in U.S. Pat. No. 9,283,278 B2 to Rodeheaver et al., which is hereby incorporated by reference.

The inverse thermosensitive polymers of the embodiments may be hydrated by mixing a suitable dry formulation of inverse thermosensitive polymers with a solvent such as, for example, water (e.g., to form an aqueous solution). Inverse thermosensitive polymers may be hydrated by any method known in the art. In some embodiments, the inverse thermosensitive polymers is present in the composition at a concentration ranging from about 5% w/w to about 85% w/w, about 10% w/w to about 20% w/w, about 15% w/w to about 25% w/w, 20% w/w to about 30% w/w, about 25% w/w to about 35% w/w, about 40% w/w to about 50%, 45% w/w to about 55%, 50% w/w to about 60%, w/w about 55% w/w to about 65% w/w, and/or w/w about 60% w/w to about 70% w/w. Additional specific examples include about 10% w/w, about 15% w/w, about 17.5% w/w, about 18% w/w, about 20% w/w, about 25% w/w, about 30% w/w, about 40% w/w, about 42% w/w, about 44% w/w, about 46% w/w, about 48% w/w, about 50% w/w, about 52% w/w, about 54% w/w, about 56% w/w, about 58% w/w, and/or about 60% w/w.

Under several embodiments, the inverse thermosensitive polymer foam formulation is an aqueous solution of one or more inverse thermosensitive polymer in an adequate concentration to exhibit reverse phase change properties, such that the solution increases markedly in viscosity (e.g., forming a strong gel when it is warmed to a preferred gel point) and decreases in viscosity when it is cooled. By selecting the type of block copolymer and an appropriate concentration in solution, this reverse phase change can be tailored to occur over a desired temperature range such that the solution is a low viscosity liquid at temperatures below that anticipated to occur in or on the body (e.g., a liquid at less than about 5-10° C., but highly viscous gel at temperatures above about 20-30° C.). In some embodiments, the inverse thermosensitive polymer foam formulation gel point is about 5° C. to about 40° C., about 5° C. to about 10° C., about 10° C. to about 15° C., about 15° C. to about 20° C., about 20° C. to about 25° C., or about 25° C. to about 30° C. Specific examples include about 12° C., about 13.5° C., about 17.4° C., about 20° C., about 25° C., about 28° C., 30° C., about 32° C., about 33° C., about 34° C., about 35° C., about 36° C., about 37° C., about 38° C., and about 40° C.

Under many embodiments, the reverse phase properties of the inverse thermosensitive polymer foam formulation provide a key advantage of the current disclosure, such that it deploys as an easier to spread (e.g., over a larger surface area; through smaller aperture) and more liquid foam that, after delivery to the body (e.g., sprayed externally, into an internal cavity), becomes a highly viscous gel (e.g., that provides a physical barrier; stabilize tissues; maintains a dressing on the body; releases therapeutic agents; and/or exerts physical tamponade). The use of an inverse thermosensitive polymer foam formulation with appropriately tailored reverse phase properties in conjunction with a suitable choice of expanding component (e.g., compressed gas or volatile liquid) provides a simple solution to these conflicting requirements. In many embodiments, the reverse phase characteristics of the inverse thermosensitive polymer solution and the properties of the expanding component are arranged such that the cooling effect, due to expansion of the expanding component as the solution is discharged, ensures that the polymer solution is in low viscosity liquid form as it exits the storage container, thereby facilitating rapid delivery to the patient. After it is delivered, the body temperature of the patient causes the inverse thermosensitive polymer solution to increase in viscosity, forming a highly viscous gel foam. An additional advantage of the reverse phase properties of the polymer solution is that the viscous gel can later be easily removed, if necessary, by cooling (e.g., by irrigation with cool or room-temperature water or normal saline) whereupon it reverts to liquid form.

Under various embodiments, the inverse thermosensitive polymer foam formulation includes one or more expanding components (e.g., compressed gas and/or volatile liquid). In many embodiments, the expanding component is one or more volatile or gaseous expanding gas and/or volatile liquid that is dissolved in, or evenly dispersed throughout, the inverse thermosensitive polymer solution. In many embodiments, when blended together the expanding component and inverse thermosensitive polymer solution form a stable and macroscopically homogeneous solution. In many embodiments, when the inverse thermosensitive polymer foam formulation is dispensed from a container, the expanding component evaporates to cause the solution to foam.

Under several embodiments, the expanding component is a compressed gas and/or volatile liquid that is dissolved within or evenly dispersed throughout the polymer solution kept under elevated pressure. The compressed expanding component expands and/or evaporates into a gaseous form due to the decrease in pressure as it is released from its storage container, thereby causing the inverse thermosensitive polymer solution to foam once dispensed. This expanding component may be any one of the many medical grade gases suitable to be delivered to the body.

Under several embodiments, this expanding component is one or more organohalide compounds, such as a fluorinated hydrocarbon (i.e., hydrofluorocarbon, or HFC) or a perfluorocarbon. For example, under some embodiments, the inverse thermosensitive polymer foam formulation is mixed with 1,1,1,2-tetrafluoroethane (i.e., norflurane, R-134a) in liquid form under a pressure of 100 pounds per square inch (psi). This mixture of polymer and hydrofluorocarbon provides a foaming polymer solution once discharged from the storage canister. Thus, under multiple embodiments, no chemical reaction with any components within the body (e.g., water) is required to cause the inverse thermosensitive polymer foam formulation to foam.

Under several embodiments, this expanding component is one or more from the following: air, hydrofluorocarbons, perfluorocarbon, fluorocarbons, carbon dioxide, hydrogen, helium, argon, nitrous oxide, nitrogen, oxygen, and mixtures thereof.

In some embodiments, the expanding component present in the inverse thermosensitive polymer foam formulation is by volume about 1% w/w to about 60% w/w, about 1% w/w to about 3% w/w, about 2% w/w to about 4% w/w, about 3% w/w to about 5% w/w, about 4% w/w to about 6% w/w, about 5% w/w to about 7% w/w, about 6% w/w to about 8% w/w, about 7% w/w to about 9% w/w, about 8% w/w to about 10% w/w, about 9% w/w to about 11% w/w, about 10% w/w to about 12% w/w, about 11% w/w to about 13% w/w, about 12% w/w to about 14% w/w, about 13% w/w to about 15% w/w, and/or about 15% w/w to about 20% w/w. Specific examples include about 1% w/w, about 2.5% w/w, about 5% w/w, about 10% w/w, and about 14% w/w.

Under many embodiments, the inverse thermosensitive polymer foam formulation is initially contained within a canister, from which it is dispensed via a valve or other mechanism. Canisters for delivering substances under pressure can in different embodiments utilize different types of expansion tanks, which under some embodiments contain one or more of the following features: aerosol, screw-on, easy click on, pierceable. Under various embodiments, the canister is different kinds of pressure-vessels with sufficient strength to contain the inverse thermosensitive polymer foam formulation (e.g., up to 120, 140, 160, 180, or 200 pounds per square inch).

These deliver the inverse thermosensitive polymer foam formulation in a pre- and/or post-foaming gel configuration. Under several embodiments, these canisters contain one or more driving gases (i.e., propellant gases). Under several embodiments, the driving gas is kept separate from the polymer to be delivered by a piston, membrane, and/or bag, so that it can transmit pressure but does not directly mix with the agent to be delivered to the body. Under some embodiments, instead of a gas, the piston is propelled by a spring, other resilient biasing means, or directly from a syringe-like applicator. Under many embodiments, the driving gas is one or more aerosol spray propellants. In some embodiments, the driving gas includes vapors that may be produced from the evaporation or sublimation of a liquid or solid substance.

In some embodiments, the driving gas is generated from a chemical reaction (e.g., an acid-base reaction). In some embodiments, there is a chemical reactant that reacts to produce a gas.

Under many embodiments, the canister is connected to a delivery applicator for applying the inverse thermosensitive polymer foam formulation (e.g., onto or into a patient). Applicators for delivering substances under pressure are well known in the art and different embodiments utilize different types. Examples include various nozzle attachments such as flat spray, quick change, extra-wide deflection, no-drip, quick-disconnect, deflection, full-cone, clog-resistant, right-angle, high-volume, square-pattern, solid-stream, high-pressure, adjustable-flow, adjustable-angle, rotating, fogging, hollow-cone, misting, ultra-fine, rotating, and/or swivel.

Under some embodiments, the applicator is designed to disperse inverse thermosensitive polymer foam over a surface area (e.g., topically over the skin). Under some embodiments, the applicator is designed to disperse inverse thermosensitive polymer foam into a body area (e.g., into a penetrating wound, into a body cavity). Under some embodiments, the applicator includes a tubing that connects to an eye shield (as seen in U.S. patent application Ser. No. 17/876,187, which is hereby incorporated herein by reference). Under some embodiments, the applicator is a needle, trocar, or other device that assists with delivery of the inverse thermosensitive polymer foam to the body. Examples include but are not limited to those disclosed in U.S. Pat. Nos. 9,616,203; 10,046,147 and 10,814,119 and U.S. Patent Publication No. 2021/0106344, each of which is hereby incorporated herein by reference.

In some embodiments, the inverse thermosensitive polymer foaming composition further includes one or more of the following additives: a humectant, a preservative, pH adjuster, therapeutic agent, and/or other additive. The humectant may be, for example, glycerin. Under various embodiments, such a humectant may be present at a concentration ranging from about 1% w/w to about 40% w/w, about 1% w/w to about 5% w/w, about 5% w/w to about 10% w/w, about 10% w/w to about 15% w/w, and/or about 15% w/w to about 25% w/w. Specific examples include about 1% w/w, about 2.5% w/w, about 5% w/w, about 10% w/w, about 12.5% w/w, and about 14% w/w.

In some embodiments, a preservative provides inhibition of bacterial, fungal, and/or other microorganisms growth within the inverse thermosensitive polymer foaming composition. In some embodiments, the preservative may be, for example, phenoxyethanol, benzalkonium chloride, PHMB, and/or chlorhexidine gluconate. Under various embodiments, such a preservative may be present at a concentration ranging from about 0.1% w/w to about 2% w/w, about 0.1% w/w to about 1% w/w, about 0.5% w/w to about 1.5% w/w, about 1% w/w to about 2% w/w, or about 0.8% w/w to about 1.2% w/w.

In some embodiments, there is no preservative. In some embodiments, the product is sterilized. Under some embodiments, the inverse thermosensitive polymer foaming composition is terminally sterilized (i.e., sterilized in its final container and/or packaging). Under some embodiments, the inverse thermosensitive polymer foaming composition is non-terminally sterilized using a step approach (e.g., sterilizing polymer solution via a heat method followed by inserting gas via a sterile filtration). In under various embodiments, the inverse thermosensitive polymer foaming composition is sterilized partially or fully by radiation (e.g., e-beam, x-ray, gamma), moist heat (i.e., steam), dry heat, chemically, and/or via gas (e.g., ethylene oxide gas, vaporized hydrogen peroxide, chlorine dioxide gas, vaporized peracetic acid, nitrogen dioxide). Under some embodiments, the inverse thermosensitive polymer foaming composition is first chilled to reduce degradation during a sterilization process (e.g., chilling before application of x-ray radiation). Under some embodiments, the canister comes in an outer pouch so as to allow for use in a sterile operating room environment (e.g., after removal from the pouch, the outside of the canister remains sterile and the product may be dropped onto a sterile operating field). Under embodiments, the outside of the canister is sterilized via chlorine dioxide, nitrogen dioxide, vaporized hydrogen peroxide, ethylene oxide, peracetic acid, e-beam, x-ray, gamma irradiation, and/or another method. In some embodiments, the composition may include one or more pH adjusters or buffers, such as sodium phosphate dibasic, citric acid, or any combination thereof. Under various embodiments, such a pH adjusters or buffers result in an inverse thermosensitive polymer foaming composition with a final pH of 4.0 to 4.0, 4.5 to 4.5, 5.0 to 6.0, 5.5 to 6.5, 6.0 to 7.0, 6.5 to 7.5, 7.0 to 8.0, 7.5 to 8.5, 8.0 to 9.0, or 8.5 to 9.5. Specific examples include pH of about 6.0%, about 6.5%, about 7.0%, about 7.5, and about 8.0.

In certain embodiments, the inverse thermosensitive polymer foaming composition may further include one or more therapeutic agents. This includes any therapeutic agent known in the art. For example, useful therapeutic agents may include, but are not limited to, anesthetics (e.g., lidocaine, bupivacaine), antifungals (e.g., griseofulvin, ketoconazole, nystatin, terbinafine), antimicrobial or antibiotic agents, hemostatics, regenerative and immune modulators (e.g., ivermectin for nerve regeneration, growth factors such as TGF-1 or platelet-derived), steroids (e.g., hydrocortisone, triamcinolone, benzocaine), other pain medications (e.g., aspirin, NSAIDs), anti-inflammatory agents, biological cells and biological agents of various types and combinations thereof.

Under some embodiments, the present disclosure contains one or more additional substances to assist with preventing, slowing, stopping, and/or treating bacterial and/or other infections (e.g., antimicrobial and antibiotic agents). These include, but are not limited to, antimicrobial agents (e.g., antibiotics), disinfectants (e.g., alcohols, aldehydes, oxidizing agents, phenolics, quaternary ammonium compounds, silver-based products, copper-based produces, and/or other disinfectants), and/or other agents (e.g., antifungals). Antibiotics are well known in the art and suitable ones for preparing the compositions of the disclosure are not limited and may be used individually or in combination. Examples include cephalosporins (e.g., cefazolin, ceftriaxone), aminoglycosides (e.g., gentamicin, tobramycin), glycopeptides (e.g., vancomycin), fluroquinolones (e.g., ciprofloxacin) and others (e.g., bacitracin, doxycycline, minocycline, neomycin, thymol). In some embodiments, the composition includes a mucoadhesive (e.g., sodium alginate).

Under embodiments, a benefit of the present disclosure is an ability of the inverse thermosensitive polymer foaming composition to maintain one or more additional substances as a dispersion and/or suspension in a stable and macroscopically homogenous solution (e.g., in a can under pressure). This is beneficial especially for additional substances that may not be partially or fully soluble in the inverse thermosensitive polymer foaming. Although not partially or fully soluble, the viscosity and/or gelation of the thermosensitive polymer foaming composition maintains a homogenous dispersion of the one or more additional substances in a stable and macroscopically homogenous solution. For example, this is in comparison to standard solutions (e.g., aqueous) in which the one or more additional substances could clump or otherwise settle to the bottom due to gravity and/or other interactive forces.

In some embodiments, the antibiotic may include, for example, gentamicin or tobramycin and may be present at a concentration ranging from about 0.1% w/w to about 2% w/w, about 0.1% w/w to about 0.5% w/w, about 0.5% w/w to about 1.0% w/w, about 1.0% w/w to about 1.5% w/w, or about 1.5% w/w to about 2.0% w/w. Specific examples include about 0.1% w/w, about 0.2% w/w, about 0.3% w/w, about 0.4% w/w, about 0.5% w/w, about 1.4% w/w, and about 2.0% w/w. In some embodiments, the antibiotic may include, for example, vancomycin and may be present at a concentration ranging from about 0.1% w/w to about 6% w/w, about 0.1% w/w to about 0.5% w/w, about 0.5% w/w to about 1.0% w/w, about 1.0% w/w to about 1.5% w/w, about 1.5% w/w to about 2.0% w/w, about 2.0% w/w to about 2.5% w/w, about 2.5% w/w to about 3.0%, about 3.0% w/w to about 3.5%, about 3.5 w/w to about 4.0%, about 4.0% w/w to about 4.5%, or about 4.5% w/w to about 5.0%. Specific examples include about 0.4% w/w, about 1.8% w/w, about 2.0% w/w, about 3.7% w/w, and about 5.0% w/w.

In some embodiments, the antibiotic is stabilized by one or more components of the rest of the inverse thermosensitive polymer foam formulation. For example, in one embodiment vancomycin is stabilized by the formulation. Vancomycin when in solution is known to be sensitive to heat and to degrade over time. In this embodiment, vancomycin in solution can be stored at longer duration outside of refrigeration, while still maintaining its efficacy, due to the benefits of storage in the inverse thermosensitive polymer foam formulation.

Under some embodiments, the present disclosure contains one or more therapeutic agents to assist with preventing, slowing, and/or stopping bleeding. These include, but are not limited to, components of the intrinsic clotting pathway (e.g., factors XI, IX, VIII); components of the extrinsic clotting pathway (e.g., transmembrane receptor tissue factor, plasma factor, factor VII/VIIa); tranexamic acid and other amino acids and their analogs; epinephrine and other vasoconstrictors; thrombin; fibrinogen; potassium ferrate; cellulose, including oxidized and/or regenerated cellulose; kaolin; smectite granules; zeolite; chitosan; sodium carboxymethylcellulose; amylopectin; microfibrillar collagen; propyl gallate; aluminum sulfate; fully acetylated poly-N-acetyl glucosamine; related substances; and other clotting agents, platelet aggregators, and substances that reduce or stop bleeding.

Under some embodiments, the present disclosure contains one or more of the previously mentioned therapeutic agents at normal concentrations for administration in the body. Under some embodiments, the present disclosure contains one or more of the previously mentioned additional substances at concentrations higher than could be used via oral and/or parenteral administration because it is delivered topically or to a body cavity. Thus, the body area has a high concentration of the additional substance, but there is a lower concentration systemically or away from that area. This allows a high concentration at the needed site but a lower concentration away from it, which minimizes systemic and/or more distal side effects. For example, an antibiotic could be administered topically to provide a very high local concentration at an area of interest, when administering such a high concentration of the agent is not possible via oral and/or parenteral route due to toxicity or other side effects.

Other embodiments of compositions encompassed by the disclosure may include other additives such as stabilizers, antioxidants, osmolality adjusting agents, chelants, calcium chelate complexes, salts, or combinations thereof. For example, in some embodiments, a stabilizer such as appropriate pharmaceutical grade surfactants such as, TWEEN or saccharides, like dextrose, may be added to the compositions of the disclosure and in some embodiments, such compositions may also include conventional pharmaceutical excipients and/or additives. For example, suitable pharmaceutical excipients may include stabilizers, antioxidants, osmolality adjusting agents, buffers, and pH adjusting agents, and suitable additives may include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or optionally, additions of calcium or sodium salts (for example, calcium chloride, calcium ascorbate, calcium gluconate or calcium lactate). Conventional nontoxic carriers may also be incorporated into such compositions and may include, for example, pharmaceutical grades of mannitol, lactose, starch, magnesium stearate, sodium saccharin, talcum, cellulose, glucose, sucrose, magnesium carbonate, and/or the like. Additional additives such as coloring agents, thickeners, lubricants, and so on may also be added to the compositions of the disclosure. In some embodiments, additives include doxycycline, bleomycin, tetracycline, povidone iodine, talc, silica (e.g., fumed silica), quinacrine, and/or a chemotherapy agent.

In some embodiments, an inverse thermosensitive polymer foam formulation consists essentially of one or more inverse thermosensitive polymer, water, and expanding component. The inverse thermo sensitive polymers are present in the composition at a concentration ranging from about 30% w/w to about 40% w/w, about 35% w/w to about 45% w/w, about 40% w/w to about 50% w/w, about 45% w/w to about % 55 w/w, and/or about 50% w/w to about % 60 w/w. Specific examples include about 40% w/w, about 42% w/w, about 44% w/w, about 46% w/w, about 48% w/w, about 50% w/w, about 52% w/w, about 54% w/w, about 56% w/w, about 58% w/w, and/or about 60% w/w. The expanding component is present in the composition at a concentration ranging from about 1-5%, about 3-7%, about 5-9%, about 7-11%, about 9-13%, about 11-15%, about 13-17%, and/or about 15-20%. Specific examples include about 2%, about 4%, about 6%, about 8%, about 10%, about 12%, about 14%, about 16%, about 18%, and about 20%. In some embodiments, such an inverse thermosensitive polymer foam formulation is produced sterile.

In some embodiments, an inverse thermosensitive polymer foam formulation consists essentially of one or more inverse thermosensitive polymer, water, expanding component, preservative, pH adjuster, and one or more therapeutic agent. The inverse thermosensitive polymers are present in the composition at a concentration ranging from about 10% w/w to about 20% w/w, about 15% w/w to about 25% w/w, about 20% w/w to about 30% w/w, about 35% w/w to about 45% w/w, and/or about 40% w/w to about 50% w/w. Specific examples include, about 14% w/w, about 16% w/w, about 18% w/w, about 20% w/w, about 22% w/w, about 24% w/w, about 26% w/w, about 28% w/w, about 30% w/w, about 32% w/w, about 34% w/w, about 36% w/w, about 38% w/w, and about 40% w/w. The expanding component is present in the composition at a concentration ranging from about 1-5%, about 3-7%, about 5-9%, about 7-11%, about 9-13%, about 11-15%, about 13-17%, and/or about 15-20%. Specific examples include about 2%, about 4%, about 6%, about 8%, about 10%, about 12%, about 14%, about 16%, about 18%, and about 20%. In some embodiments, such an inverse thermosensitive polymer foam formulation is produced sterilized. The preservative is present in the composition at a concentration ranging from about 0.25-0.75% w/w, about 0.5-1% w/w, about 0.75-1.25% w/w, about 1-1.5% w/w, about 1.25-1.75% w/w, about 1.5-2% w/w, about 1.75-2.25% w/w, about 2.5-3% w/w, and/or about 3-5% w/w. Specific examples include about 0.5% w/w, about 1% w/w, about 1.5% w/w, about 2% w/w, about 3% w/w, about 4% w/w, and about 5% w/w. The pH adjuster is present in the composition at a pH ranging from about 5-5.5, about 5.25-5.75, about 5.5-6, about 5.75-6.25, about 6-6.5, about 6.25-6.75, about 6.5-7, about 6.75-7.25, about 7-7.5, about 7.25-7.75, about 7.5-8, about 7.75-8.25, about 8-8.5, about 8.25-8.75, and/or about 8.5-9. Specific examples include about 5, about 5.5, about 6, about 6.5, about 7, about 7.5, about 8, about 8.5, and about 9. One or more therapeutic agent is present in the composition at an individual concentration ranging from about 0.01-1% w/w, about 1-2% w/w, about 2-3% w/w, about 3-4% w/w, about 4-5% w/w, about 5-6% w/w, about 6-7% w/w, about 7-8% w/w, about 8- 9% w/w, about 9-10% w/w, and/or about 10-12% w/w. Specific examples include about 0.1% w/w, about 0.4% w/w, about 0.5% w/w, about 0.9% w/w, about 1% w/w, about 1.5% w/w, about 2% w/w, about 3% w/w, about 3.7%, about 4% w/w, about 5% w/w, about 6% w/w, about 7% w/w, about 8% w/w, about 9% w/w, and about 10% w/w.

In some embodiments, an inverse thermosensitive polymer foam formulation consists essentially of one or more inverse thermosensitive polymer, water, expanding component, preservative, pH adjuster, and humectant. The inverse thermosensitive polymers are present in the composition at a concentration ranging from about 10% w/w to about 20% w/w, about 15% w/w to about 25% w/w, about 20% w/w to about 30% w/w, about 35% w/w to about 45% w/w, and/or about 40% w/w to about 50% w/w. Specific examples include, about 14% w/w, about 16% w/w, about 17.5%, about 18% w/w, about 20% w/w, about 22% w/w, about 24% w/w, about 26% w/w, about 28% w/w, about 30% w/w, about 32% w/w, about 34% w/w, about 36% w/w, about 38% w/w, and about 40% w/w. The expanding component is present in the composition at a concentration ranging from about 1-5%, about 3-7%, about 5-9%, about 7-11%, about 9-13%, about 11-15%, about 13-17%, and/or about 15-20%. Specific examples include about 2%, about 4%, about 6%, about 8%, about 10%, about 12%, about 14%, about 16%, about 18%, and about 20%. In some embodiments, such an inverse thermosensitive polymer foam formulation is produced sterilized. The preservative is present in the composition at a concentration ranging from about 0.25-0.75% w/w, about 0.5-1% w/w, about 0.75-1.25% w/w, about 1-1.5% w/w, about 1.25-1.75% w/w, about 1.5-2% w/w, about 1.75-2.25% w/w, about 2.5- 3% w/w, and/or about 3-5% w/w. Specific examples include about 0.5% w/w, about 1% w/w, about 1.5% w/w, about 2% w/w, about 3% w/w, about 4% w/w, and about 5% w/w. The pH adjuster is present in the composition at a pH ranging from about 5-5.5, about 5.25-5.75, about 5.5-6, about 5.75-6.25, about 6-6.5, about 6.25-6.75, about 6.5-7, about 6.75-7.25, about 7-7.5, about 7.25-7.75, about 7.5-8, about 7.75-8.25, about 8-8.5, about 8.25-8.75, and/or about 8.5-9. Specific examples include about 5, about 5.5, about 6, about 6.5, about 7, about 7.5, about 8, about 8.5, and about 9. The humectant is present in the composition at a concentration ranging from about 0.1% w/w to about 10% w/w, 5% w/w to about 15% w/w, 10% w/w to about 20% w/w, about 15% w/w to about 25% w/w, about 20% w/w to about 30% w/w, about 35% w/w to about 45% w/w, and/or about 40% w/w to about 50% w/w. Specific examples include, about 4% w/w, about 6% w/w, 8% w/w, 10% w/w, 12% w/w, 12.5% w/w, 14% w/w, about 16% w/w, about 17.5%, about 18% w/w, about 20% w/w, about 22% w/w, about 24% w/w, about 26% w/w, about 28% w/w, about 30% w/w, about 32% w/w, about 34% w/w, about 36% w/w, about 38% w/w, and about 40% w/w.

In some embodiments, an inverse thermosensitive polymer foam formulation consists essentially of one or more inverse thermosensitive polymer, water, expanding component, pH adjuster, and one or more therapeutic agent. The inverse thermosensitive polymers are present in the composition at a concentration ranging from about 10% w/w to about 20% w/w, about 15% w/w to about 25% w/w, about 20% w/w to about 30% w/w, about 35% w/w to about 45% w/w, and/or about 40% w/w to about 50% w/w. Specific examples include, about 14% w/w, about 16% w/w, about 18% w/w, about 20% w/w, about 22% w/w, about 24% w/w, about 26% w/w, about 28% w/w, about 30% w/w, about 32% w/w, about 34% w/w, about 36% w/w, about 38% w/w, and about 40% w/w. The expanding component is present in the composition at a concentration ranging from about 0.1-3%, about 1-5%, about 3-7%, about 5-9%, about 7-11%, about 9-13%, about 11-15%, about 13-17%, and/or about 15-20%. Specific examples include about 0.1%, about 0.25%, about 0.5%, about 1%, about 1.5%, about 2%, about 2.5%, about 4%, about 6%, about 8%, about 10%, about 12%, about 14%, about 16%, about 18%, and about 20%. In some embodiments, such an inverse thermosensitive polymer foam formulation is produced sterilized. The pH adjuster is present in the composition at a pH ranging from about 5-5.5, about 5.25-5.75, about 5.5-6, about 5.75-6.25, about 6-6.5, about 6.25-6.75, about 6.5-7, about 6.75-7.25, about 7-7.5, about 7.25-7.75, about 7.5-8, about 7.75-8.25, about 8-8.5, about 8.25-8.75, and/or about 8.5-9. Specific examples include about 5, about 5.5, about 6, about 6.5, about 7, about 7.5, about 8, about 8.5, and about 9. One or more therapeutic agent is present in the composition at an individual concentration ranging from about 0.01-1% w/w, about 1-2% w/w, about 2-3% w/w, about 3-4% w/w, about 4-5% w/w, about 5-6% w/w, about 6-7% w/w, about 7-8% w/w, about 8-9% w/w, about 9-10% w/w, and/or about 10-12% w/w. Specific examples include about 0.1% w/w, about 0.4% w/w, about 0.5% w/w, about 0.9% w/w, about 1% w/w, about 1.5% w/w, about 2% w/w, about 3% w/w, about 3.7%, about 4% w/w, about 5% w/w, about 6% w/w, about 7% w/w, about 8% w/w, about 9% w/w, and about 10% w/w. In some embodiments, such an inverse thermosensitive polymer foam formulation is produced sterile.

The methods described herein may be useful for treating patients exhibiting a number of indications or suffering from any number of conditions. Under several embodiments, examples include the provision of hemostasis, anesthesia, analgesia, antifungal, antibacterial, antimicrobial, environmental stabilization (e.g., pH regulation), wound healing, regeneration of wounded tissue, immune modulation, and/or antibiofilm.

Examples of such conditions include but are not limited to burns, abrasions, cuts, scrapes, surgical incisions, and/or other denuding tissue injuries. In some embodiments, such conditions are caused by chemical and biological threats (e.g., sulfur mustard dermal injuries). In some embodiments, the compositions of the disclosure may be used to treat chronic wounds. Examples of such conditions include but are not limited to venous ulcers, diabetic ulcers, arterial ulcers, pressure ulcers (e.g., decubitus ulcers), radiation ulcers, traumatic wounds, and/or complicated non-healing wounds.

In some embodiments, the method may include applying an inverse thermosensitive polymer foam formulation topically to the body. In some embodiments, the method may include applying an inverse thermosensitive polymer foam formulation into the body (e.g., into a potential space, into a body cavity, into an organ). In some embodiments, the method may include applying an inverse thermosensitive polymer foam formulation directly to a non-human surface (e.g., including non-pharmaceutical applications). Under some embodiments, the inverse thermosensitive polymer foam formulation is applied directly to an inanimate object, surgical instrument, operating room surface, medical device meant to be use on and/or inserted into a patient.

In embodiments, the device delivers a substantially uniform therapeutic coating of inverse thermosensitive polymer foam formulation. The thickness of a therapeutic coating of the composition when applied may vary in accordance with the size of a wound, the time available to apply the composition, the amount of composition available and other variables. For example, in various embodiments, the thickness of the applied compositions may be about 0.1 inch, about 0.25 inch, about 0.5 inch, about 0.75 inch, about 1 inch, about 1.25 inch, about 1.5 inch, about 1.75 inch, or about 2 inches.

In some embodiments, the disclosure includes a dressing for maintaining an inverse thermosensitive polymer foam formulation on and/or in the body. A wide range of medical dressing options may be used. Many such dressings assist with healing injured and/or sick tissue. In some embodiments, the disclosure includes an adapter for inserting an inverse thermosensitive polymer foam formulation directly into a body cavity (e.g., a penetrating gunshot wound). Under some embodiments, it provides a temporary barrier (e.g., <24 hours) to bacterial penetration with included antimicrobials to prevent bacterial colonization. Under some embodiments, its use is indicated for penetrating soft tissue injuries that are at high-risk for infection. Examples of such wounds include, but are not limited to, those with the following risk factors: battlefield injury; anticipated delay in treatment; concomitant fracture; gross wound contamination; high-energy projectile; large and/or complex wounds; and/or significant tissue devitalization. Under some embodiments, included antimicrobials may be tailored to cover bacterial contaminants from salt and/or freshwater environments (e.g., ciprofloxacin to cover for vibrio species).

Under some of embodiments, the inverse thermosensitive polymer foam formulation can be cleared by the body, such that there is no need for subsequent physical removal (e.g., resorbable). In other embodiments, its thermoreversible nature is used to facilitate removal by using room temperature and/or chilled liquid to remove it. Various embodiments of the present disclosure have one or more of the following characteristics: it is stable without need for refrigeration; it maintains activity under environmental extremes experienced in military operations; it prevents bacterial adhesion and/or biofilm formation; it inhibits drug-resistance mechanisms in multidrug-resistant strains of bacteria; it is not exothermic and/or has minimal risk of iatrogenic thermal injury to organs; it is transparent; and/or it does not discolor tissues.

From the foregoing, it can be seen that the present disclosure provides systems and methods relating to inverse thermosensitive polymer foam formulations within animals, especially humans. Examples have been presented herein which demonstrate the features and advantages of certain inverse thermosensitive polymer foam formulations representing embodiments of the disclosure. These examples are not intended to limit the scope of the disclosure to any specific formulations of synthetic polymers, gases, or volatile liquids and/or concentrations or combinations thereof. It will be apparent to those skilled in the art that formulations containing other poloxamers, other synthetic polymers, other expanding gases, and optionally other components including compounds intended to build and stabilize the foam may also be used.

Moreover, it should also be apparent that the device can be made in varying lengths, sizes, pressures, and capacities, and the precise composition of the inverse thermosensitive polymer foam formulation may be varied appropriately to treat adults, children, and infants. While the embodiments of the disclosure has been described with a certain degree of particularity, it is manifest that many changes may be made in the details of construction and the arrangement of components without departing from the spirit and scope of this disclosure. It is understood that the disclosure is not limited to the embodiments set forth herein for purposes of exemplification and that elements of certain embodiments can be combined with elements of other embodiments. Additional objects, advantages, and novel features of the disclosure will be set forth in the description which follows, and will become apparent to those skilled in the art upon examination of the following detailed description and figures. It should be understood that not all of the features described need be incorporated into a given system or method.

The present disclosure may be embodied in other specific forms without departing from the spirit or essential attributes thereof. This disclosure encompasses all combinations of the different aspects of the disclosure noted herein. It is understood that any and all embodiments of the present disclosure may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment. While particular embodiments have been described, it is not intended that the disclosure be limited thereto, as it is intended that the disclosure be as broad in scope as the art will allow.

BRIEF DESCRIPTION OF THE DRAWINGS

Subject matter hereof may be more completely understood in consideration of the following detailed description of various embodiments in connection with the accompanying figures, in which:

FIG. 4 is a sample table of different inverse thermosensitive polymer foam formulations made in accordance with several embodiments.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
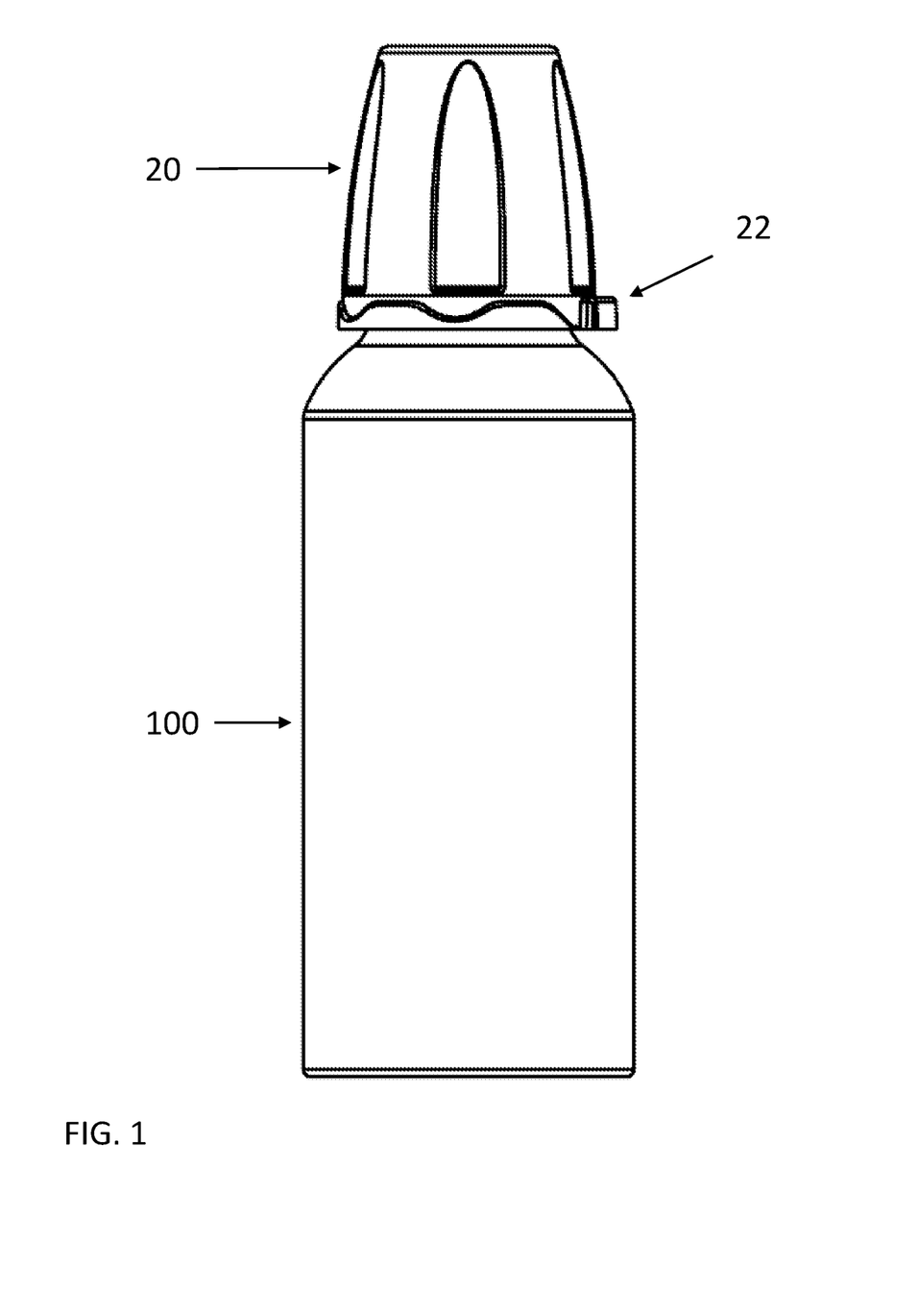
FIG. 1 is an isometric view of part of a system to deliver inverse thermosensitive polymer foam formulations to the body in accordance with one embodiment.

Referring to the drawings, FIG. 1 illustrates a delivery container suitable for holding and delivery of an inverse thermosensitive polymer foam formulation under one embodiment. The body of the delivery container includes canister 100. On top is cap 20, which includes removal tab 22. In many embodiments, removal tab 22 is a tamper-evident and/or tamper-proof seal. Once removal tab 22 has been removed, cap 20 may be removed from canister 100.

Figure 2:
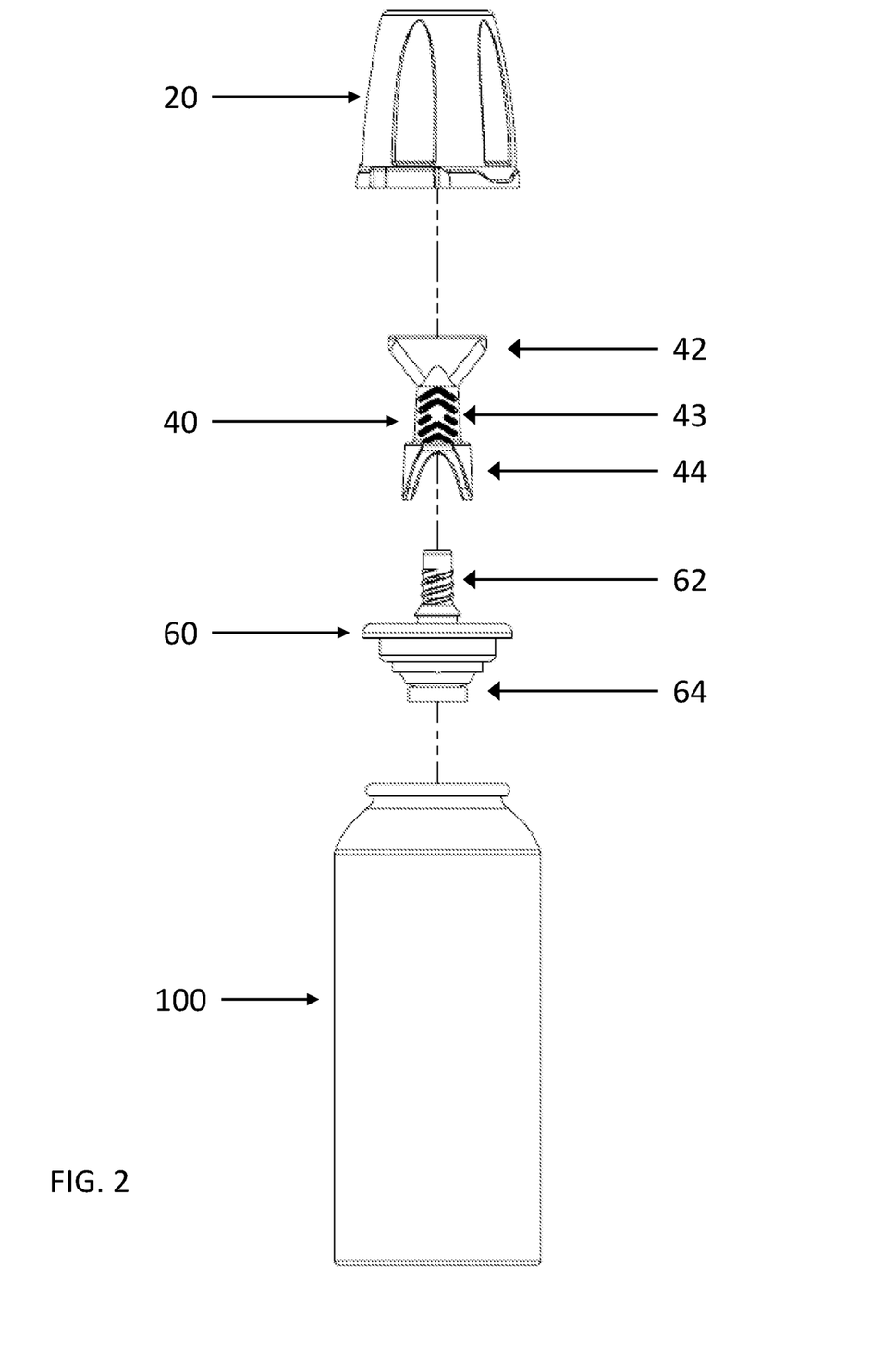
FIG. 2 is an isometric expanded assembly view of part of a system to deliver inverse thermosensitive polymer foam formulations to the body in accordance with one embodiment.

FIG. 2 shows an expanded assembly view. The canister 100 is connected to valve 60 containing release mechanism 64. The canister, valve, and release mechanism when combined can together withstand an internal pressure (e.g., from the inverse thermosensitive polymer foam formulation inside). Release mechanism 64 is opened, in this embodiment, by lateral pressure onto release actuator 62. Other embodiments include opening of release mechanism 64 via a lever, button, pull tab, twist, push, pull, other manually-activated releasing mechanism, and/or electronic means. In this embodiment, applicator 40 connects to valve 60 by reversibly screwing onto release actuator 62. Other embodiments include non-reversible connection and/or direct connection to another part of valve 60. Applicator 40 contains spreader 42, which in this embodiment is engineered to optimally disperse inverse thermosensitive polymer foam over a surface area, applicator control 43, where a user in this embodiment presses (e.g., with a finger) to dispense foam, and phalanges 44, which prevent foam application unless applicator 40 is pressed with force in an upright plane perpendicular to a plane intersecting both phalanges 44. Finally, cap 20 is placed on top to contain applicator 40 and connect with canister 100 and/or valve 60.

Figure 3:
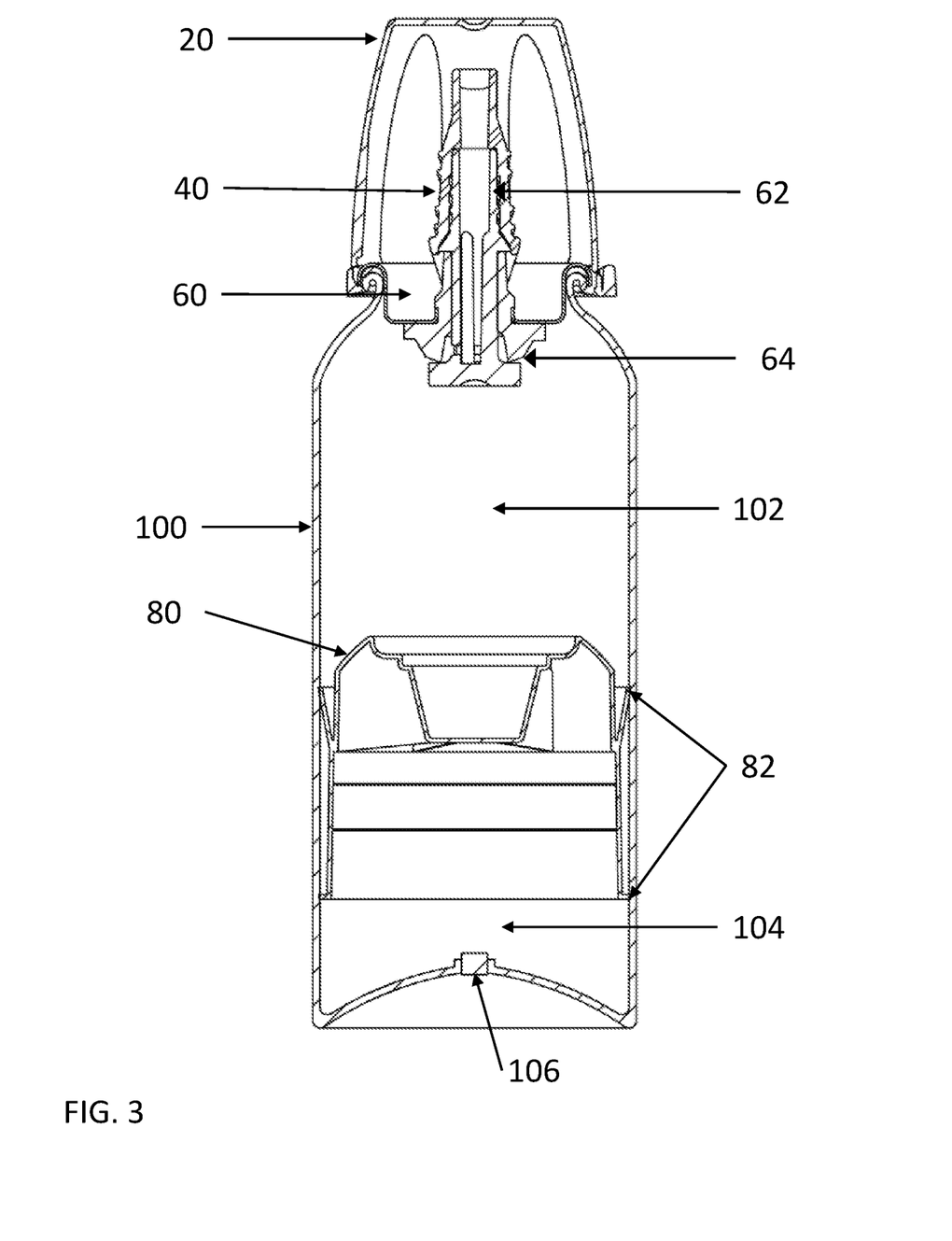
FIG. 3 is a cross section view of part of a system to deliver inverse thermosensitive polymer foam formulations to the body in accordance with one embodiment, as assembled prior to use.

FIG. 3 shows a cross sectional view of one embodiment. This view shows that the vessel is internally divided into an upper space 102 and a lower space 104 by a freely-moving piston 80. Piston 80 bears one or more pressure-tight seals 82 that prevents movement of liquid or gas from one space into the other. Under different embodiments, seal 82 is integral to the piston or is created using a separate sealing component such as an O-ring. Release mechanism 64 opens into applicator 40. Canister 100 also contains a gas-tight valve 106 or other similar means (e.g., replaceable bung) to allow propellant (e.g., gas or volatile liquid) to be introduced into lower space 104. When the delivery container is fully assembled and ready for use, upper space 102 contains the inverse thermosensitive polymer foam formulation. In many embodiments, this formulation contains one or more compressed gases or volatile liquids (the "expanding gas") which causes the inverse thermosensitive polymer foam formulation to foam when released from the delivery container. The lower space 104 also contains one or more compressed gases or volatile liquids (the "driving gas"). The driving gas may be either introduced into the lower space of the delivery container prior to use (e.g., at the time the container is initially filled with the inverse thermosensitive polymer foam formulation) or it may be introduced into the lower space of the delivery container at the time of use (e.g., by connection to an external source such as compressed air supply or a pressurized gas cylinder).

A key feature of this embodiment is that the driving gas in the lower space 104 is physically separated from the inverse thermosensitive polymer foam formulation in the upper space 102. An advantage of this embodiment is that the pressure of the driving gas in the lower space 104 can be arranged to always exceed the pressure of the expanding gas in the upper space 102 until the contents of upper space 102 have been sufficiently discharged from the container, thereby maintaining the expanding gas in a compressed form until the inverse thermosensitive polymer foam formulation has been released via the valve mechanism 64 into applicator 40. Under some embodiments, this may be achieved by having the expanding and driving gases be the same compressed gas and/or volatile liquid.

Unlike the embodiment described in relation to FIGS. 3, under some embodiments, there is no piston 80 (or related membrane, and/or bag) to physically separate space 102 from space 104 (and thus the expanding and driving gases). Under these embodiments, there is no driving gas and instead the inverse thermosensitive polymer foam formulation is propelled out of the container by the expanding gas only.

Under some embodiments, the inverse thermosensitive polymer foam formulation is integrated into delivery devices with additional capabilities, such as those described in U.S. patent application Ser. No. 17/876,187, U.S. Pat. Nos. 9,616,203; 10,046,147 and 10,814,119 and U.S. Patent Publication No. 2021/0106344, previously incorporated herein by reference. Under some embodiments, the delivery container is partially or completely integrated into the delivery device, so as to minimize parts and/or size.

EXAMPLES

The following examples more particularly describe certain embodiments of disclosure but are intended for illustrative purposes only, since modifications and variations will be apparent to those skilled in the art.

For a series of experiments to study the physical properties of the foaming inverse thermosensitive polymer foam formulation, sample mixtures were made and deployed to test deployment characteristics.

Example 1: Resultant Example Foam Formulations

FIG. 4 shows a sample table of different inverse thermosensitive polymer foam formulations made in accordance with several embodiments.

In embodiments a pressurized inverse thermosensitive polymer foam formulation can be configured to be stored in a valved container designed to maintain the formulation under pressure and to dispense the formulation upon opening a valve of the valve container. The formulation can include an aqueous solution of a copolymer of ethylene oxide and propylene oxide about 15% to about 25% w/w of the formulation configured to undergo a reverse phase change from a liquid to a gel at about 10° C. to about 15° C. The formulation can further include a preservative, a pH adjuster resulting in a pH of the formulation of about 6.25 to 6.75 and an expanding component that is a liquified hydrofluorocarbon gas comprising about 9% to about 13% of a total mass of the formulation. The formulation can be a stable and macroscopically homogenous solution. The formulation can be configured to be deployed from the container such that the liquified hydrofluorocarbon gas causes the formulation to foam after the formulation is dispensed from the container such that the formulation is applied topically.

In some embodiments, the formulation is further configured to be deployed from the valve container by a driving gas that is separated from the formulation in the valved container by a piston.

In some embodiments, the copolymer of ethylene oxide and propylene oxide is a poloxamer selected from the group consisting of: P188, P237, P338 and P407.

In some embodiments, the aqueous solution of the copolymer of ethylene oxide and propylene oxide is about 17.5% w/w of the formulation.

In some embodiments, the formulation further includes a humectant.

In some embodiments, the humectant is glycerin.

In some embodiments, the humectant is about 8.5% to about 17.5% w/w of the formulation In some embodiments, the humectant is about 12.5% w/w of the formulation.

In some embodiments, the preservative is phenoxyethanol.

In some embodiments, the preservative is about 1% w/w of the formulation.

In some embodiments, the pH adjuster is a phosphate buffer.

In some embodiments, the formulation is configured to be deployed from the container through an applicator tip having a removable cap.

In embodiments, a pressurized inverse thermosensitive polymer foam formulation is configured to be stored in a valved container designed to maintain the formulation under pressure and to dispense the formulation upon opening a valve of the valve container. The formulation can include an aqueous solution of a copolymer of ethylene oxide and propylene oxide configured to undergo a reverse phase change from a liquid to a gel. The formulation can further include a preservative, a pH adjuster and an expanding component that is a liquified hydrofluorocarbon gas. The formulation can be a stable and macroscopically homogenous solution. The formulation can be configured to be deployed from the container such that the liquified hydrofluorocarbon gas causes the formulation to foam after the formulation is dispensed from the container and the formulation applied topically. The formulation can be configured to initially be deployed from the container at a lower viscosity to spread more easily and become more viscous upon contact with the body.

In some embodiments, the copolymer of ethylene oxide and propylene oxide is about 15% to about 25% w/w of the formulation.

In some embodiments, the formulation further includes a humectant.

In some embodiments, the humectant is glycerin.

In some embodiments, the humectant is about 8.5% to about 17.5% w/w of the formulation In some embodiments, the humectant is about 12.5% w/w of the formulation.

In some embodiments, the pH adjuster results in a pH of the formulation of about 6.25 to 6.75.

In some embodiments, the liquefied hydrofluorocarbon gas comprises about 9% to 13% of a total mass of the formulation.

In embodiments, a pressurized valve container can include a container including a valve and a pressurized inverse thermosensitive polymer foam formulation stored in the container. The container can be configured to maintain the formulation under pressure and dispense the formulation upon opening the valve. The formulation can include an aqueous solution of a copolymer of ethylene oxide and propylene oxide about 15% to about 25% w/w of the formulation configured to undergo a reverse phase change from a liquid to a gel at about 10° C. to about 20° C. The formulation can further include, a preservative, a pH adjuster resulting in a pH of the formulation of about 6.25 to 6.75 and an expanding component that is a liquified hydrofluorocarbon gas comprising about 9% to about 13% of a total mass of the formulation. The formulation can be a stable and macroscopically homogenous solution. The container can be configured to deploy the formulation such that the liquified hydrofluorocarbon gas causes the formulation to foam after the formulation is dispensed from the container such that the formulation is applied topically.

In some embodiments, the container further includes a piston separating the pressurized inverse thermosensitive polymer foam formulation from a driving gas.

In some embodiments, the driving gas is the same liquified hydrofluorocarbon gas as the expanding component.

In some embodiments, the container further includes an applicator tip with a removable cap. In some embodiments, the applicator tip includes a spreader configured to disperse the foam over a surface area.

In some embodiments, the formulation further includes a humectant.

In some embodiments, the humectant is glycerin.

In some embodiments, the humectant is about 8.5% to about 17.5% w/w of the formulation In some embodiments, the humectant is about 12.5% w/w of the formulation.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. A pressurized inverse thermosensitive polymer foam formulation configured to be stored in a valved container designed to maintain the formulation under pressure and dispense the formulation upon opening a valve of the valved container, the formulation comprising:
   an aqueous solution of a copolymer of ethylene oxide and propylene oxide, wherein the aqueous solution is configured to undergo a reverse phase change from a liquid to a gel;
   one or more antibiotics, the one or more antibiotics including vancomycin at a concentration between about 0.1% w/w/to about 6.0% w/w;
   a preservative;
   a pH adjuster; and
   an expanding component that is a liquified hydrofluorocarbon gas, wherein
      the formulation comprises a stable and macroscopically homogenous solution,
      the formulation is configured to be deployed from the container such that the liquified hydrofluorocarbon gas causes the formulation to foam after the formulation is dispensed from the container,
      the formulation is configured to be applied topically, and
      the formulation is configured to initially be deployed from the container at a lower viscosity to spread more easily and becomes more viscous upon contact with the body.

2. The pressurized inverse thermosensitive polymer foam formulation of claim 1, further comprising a humectant.

3. The pressurized inverse thermosensitive polymer foam formulation of claim 1, wherein the preservative is phenoxyethanol.

4. The pressurized inverse thermosensitive polymer foam formulation of claim 1, wherein the pH adjuster is a phosphate buffer.

5. The pressurized inverse thermosensitive polymer foam formulation of claim 1, wherein the pH adjuster results in a pH of the formulation of about 6.25 to 6.75.

6. A pressurized valve container, comprising:
   a container including a valve;
   a pressurized inverse thermosensitive polymer foam formulation stored in the container, the container configured to maintain the formulation under pressure and dispense the formulation upon opening the valve, the formulation comprising:

an aqueous solution of a copolymer of ethylene oxide and propylene oxide, wherein the aqueous solution is configured to undergo a reverse phase change from a liquid to a gel;

one or more antibiotics, the one or more antibiotics including vancomycin at a concentration between about 0.1% w/w to about 6.0% w/w;

a preservative;

a pH adjuster; and an expanding component that is a liquified hydrofluorocarbon gas, wherein the formulation comprises a stable and macroscopically homogenous solution, wherein the container is configured to deploy the formulation such that the liquified hydrofluorocarbon gas causes the formulation to foam after the formulation is dispensed from the container, the formulation is configured to be applied topically following deployment from the container, and the formulation is configured to initially be deployed from the container at a lower viscosity to spread more easily and becomes more viscous upon contact with the body.

7. The pressurized valved container of claim 6, further comprising a piston separating the pressurized inverse thermosensitive polymer foam formulation from a driving gas.

8. The pressurized valved container of claim 7, wherein the driving gas is the same liquified hydrofluorocarbon gas as the expanding component.

9. The pressurized valved container of claim 6, further comprising an applicator tip including a spreader configured to disperse the foam over a surface area.

10. The pressurized inverse thermosensitive polymer foam formulation of claim 1, wherein the one or more antibiotics further includes one or more of the following: cephalosporin, aminoglycoside, glycopeptide, fluroquinolone, bacitracin, doxycycline, minocycline, neomycin, and thymol.

11. The pressurized inverse thermosensitive polymer foam formulation of claim 1, wherein the one or more antibiotics includes gentamicin or tobramycin at a concentration between about 0.1% w/w to about 2% w/w.

12. The pressurized inverse thermosensitive polymer foam formulation of claim 1, wherein the one or more antibiotics includes both vancomycin and an aminoglycoside.

13. The pressurized inverse thermosensitive polymer foam formulation of claim 12, wherein the aminoglycoside has a concentration between about 0.1% w/w to about 2% w/w.

14. The pressurized inverse thermosensitive polymer foam formulation of claim 1, wherein the one or more antibiotics is stabilized by one or more components of the rest of the inverse thermosensitive polymer foam formulation.

15. The pressurized inverse thermosensitive polymer foam formulation of claim 2, wherein the humectant is glycerin.

* * * * *